United States Patent
Lemchen

(10) Patent No.: US 9,516,207 B2
(45) Date of Patent: Dec. 6, 2016

(54) EXAM-CAM ROBOTIC SYSTEMS AND METHODS

(76) Inventor: Marc S. Lemchen, New York, NY (US)

(*) Notice: Subject to any disclaimer, the term of this patent is extended or adjusted under 35 U.S.C. 154(b) by 1149 days.

(21) Appl. No.: 13/168,688

(22) Filed: Jun. 24, 2011

(65) Prior Publication Data
US 2011/0316994 A1 Dec. 29, 2011

Related U.S. Application Data

(60) Provisional application No. 61/358,356, filed on Jun. 24, 210.

(51) Int. Cl.
| | |
|---|---|
| *A61C 1/08* | (2006.01) |
| *A61G 15/14* | (2006.01) |
| *B25J 9/02* | (2006.01) |
| *H04N 5/232* | (2006.01) |
| *A61C 9/00* | (2006.01) |

(52) U.S. Cl.
CPC .............. *H04N 5/232* (2013.01); *A61C 1/082* (2013.01); *A61C 9/004* (2013.01); *A61C 9/008* (2013.01); *A61G 15/14* (2013.01); *B25J 9/02* (2013.01)

(58) Field of Classification Search
None
See application file for complete search history.

(56) References Cited

U.S. PATENT DOCUMENTS

| | | | | |
|---|---|---|---|---|
| 7,772,796 | B2 * | 8/2010 | Farritor | A61B 1/00158 104/138.1 |
| 2005/0084816 | A1 * | 4/2005 | Mehdizadeh | 433/29 |
| 2005/0186533 | A1 * | 8/2005 | Cohen | 433/98 |
| 2007/0265495 | A1 * | 11/2007 | Vayser | 600/109 |
| 2009/0061381 | A1 * | 3/2009 | Durbin et al. | 433/24 |
| 2009/0088634 | A1 * | 4/2009 | Zhao et al. | 600/427 |
| 2009/0227998 | A1 * | 9/2009 | Aljuri et al. | 606/13 |
| 2009/0253095 | A1 * | 10/2009 | Salcedo et al. | 433/75 |
| 2010/0331855 | A1 * | 12/2010 | Zhao et al. | 606/130 |

* cited by examiner

*Primary Examiner* — Joseph Ustaris
*Assistant Examiner* — William Adrovel
(74) *Attorney, Agent, or Firm* — Marcus C. Dawes; Daniel L. Dawes

(57) ABSTRACT

The illustrated embodiment of the invention encompasses an apparatus for intraoral imaging of teeth of a patient which includes a camera, a robotic arm coupled to the camera which arm is capable of rotating the camera for selectively positioning the camera into the mouth of the patient, at least one sensor coupled to arm to sense the relative position of the teeth and/or mouth with respect to the camera, and a controller coupled to the at least one sensor and arm for controlling the arm to avoid any collision between the teeth or the interior of the mouth and the camera and/or arm, where the controller further selectively moves the arm to track any movement of the patient to keep the camera in a constant relative position with respect to the teeth or mouth.

11 Claims, 2 Drawing Sheets

EXAM-CAM ROBOTIC SYSTEMS AND METHODS

RELATED APPLICATIONS

The present application is related to U.S. Provisional Patent Application, Ser. No. 61/358,356, filed on Jun. 24, 2010, which is incorporated herein by reference and to which priority is claimed pursuant to 35 USC 119.

FIELD OF THE TECHNOLOGY

The disclosure relates to apparatus and methods for dental examination and practice using camera vision.

BRIEF SUMMARY

The illustrated embodiment of the invention encompasses an apparatus for intraoral imaging of teeth of a patient which includes a camera, a robotic arm coupled to the camera which arm is capable of rotating the camera for selectively positioning the camera into the mouth of the patient, least one sensor coupled to arm to sense the relative position of the teeth and/or mouth with respect to the camera, and a controller coupled to the at least one sensor and arm for controlling the arm to avoid any collision between the teeth or the interior of the mouth and the camera and/or arm, where the controller further selectively moves the arm to track any movement of the patient to keep the camera in a constant relative position with respect to the teeth or mouth.

The apparatus may further include a lighting system or a light source(s) mounted on the distal end of the arm for providing intraoral illumination for the camera.

The apparatus may further include a joy stick coupled to the controller to allow for manual control of the camera.

The apparatus may further include a headset peripheral coupled to the controller, which headset peripheral programmably learns head and muscle movements, or facial muscle activation of a user to control translational and rotational movement the arm or camera.

The apparatus may further include a sensor for tracking the eye movements of a user for control of movement of the arm or camera.

The apparatus may further comprise a gripper, and/or tool coupled to arm. The tool may be any kind of dental tool now known or later devised, including a rotary dental instrument, a dental laser or an abrasion tool to cut tooth material or trim soft tissue. The apparatus includes any kind of mechanical clasp to grasp a buccal and/or lingual surface of the tooth close to the gingival margin or at a predetermined distance away from an operative site.

The controller or computer aligns the camera to match a previously scanned image of an area in view using a previously scanned image originally captured on a CBCT, laser or optical scanner, or with a dental impression.

The apparatus may further include a gripper, and/or tool coupled to arm, and where the controller robotically controls the camera, gripper and/or tool to perform a dental operation. The camera, gripper and/or tool is robotically controlled to prepare a tooth for a restoration, reshape an edge, or adjust a bite using data from a previously prepared three dimensional digital scan of the tooth. The controller robotically controls the camera, gripper and/or tool to adjust orthodontic wires with the gripper, place braces, apply coatings, or to drill bone for precise implant placement without a cad/cam template to guide placement by allowing the drilling to be precisely placed.

The apparatus may further include a gripper, and/or tool coupled to arm, and where the controller robotically controls the camera, gripper and/or tool to perform robotic occlusal and incisal adjustment. The gripper is controlled to grasp a buccal and lingual surface of a tooth and line up with a previously prepared tooth/anatomy image. The camera, gripper and/or tool are controlled to perform robotic occlusal and incisal adjustment by use of the tool as a robotic shaper which adjusts a tooth based upon precise three dimensional digital occlusal analysis to mill the tooth or teeth to a specific shape. The shape can be created by control of the joy stick or by preloaded templates to produce a shape suitable for a restoration to be placed. There may be a library of shapes and prefabricated restorations, which once placed, may be adjusted by the system to a correct occlusion or bite.

The apparatus may further include a joy stick or headset peripheral coupled to the controller, where the controller robotically controls the camera and arm as operated by the joy stick or headset peripheral to allow a user to visualize the patient's mouth just as if the user were sitting next to the patient.

The controller robotically controls the camera to allow the user to visualize the patient's mouth at a selected magnification with user-customizable imaging enhancements.

The controller robotically controls the gripper or tool to perform tooth adjustment or tooth preparation, or implant preparation or implant placement. The controller robotically controls the gripper to hold a buccal or lingual surface of a tooth mesial and or distal of the tooth or of an area to be adjusted or prepared, while sensing and adjusting for any patient movement, using the camera to align a previously prepared image of the tooth with the actual tooth as imaged by the camera and correlating the images to the gripper and the tool, which includes a dental cutting device, rotary, laser, abrasion-dental device to prepare the tooth or area or using the camera to rescan a prepared tooth to assure it matches intended preparation or adjustment.

The controller is coupled to a communication network or the internee to send data to a remote lab or milling machine to fabricate a restoration to fit a preparation without additional scan or impression to adjust the restoration.

The controller is arranged and configured to control the arm and camera to automatically scan the patient's dental arch to produce a photographic three dimensional scan.

The illustrated embodiments also include any and all methods for operating any one of the embodiments of apparatus disclosed above.

The illustrated embodiments also include any and all sets of instructions stored on a tangible medium for controlling a computer or controller in any one of the apparatus described above or for performing any of the methods mentioned above.

While the apparatus and method has or be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the of embodiments as defined by the claims may be broader than the illustrated embodiments described below.

DETAILED DESCRIPTION OF THE PREFERRED EMBODIMENTS

Figure 1:
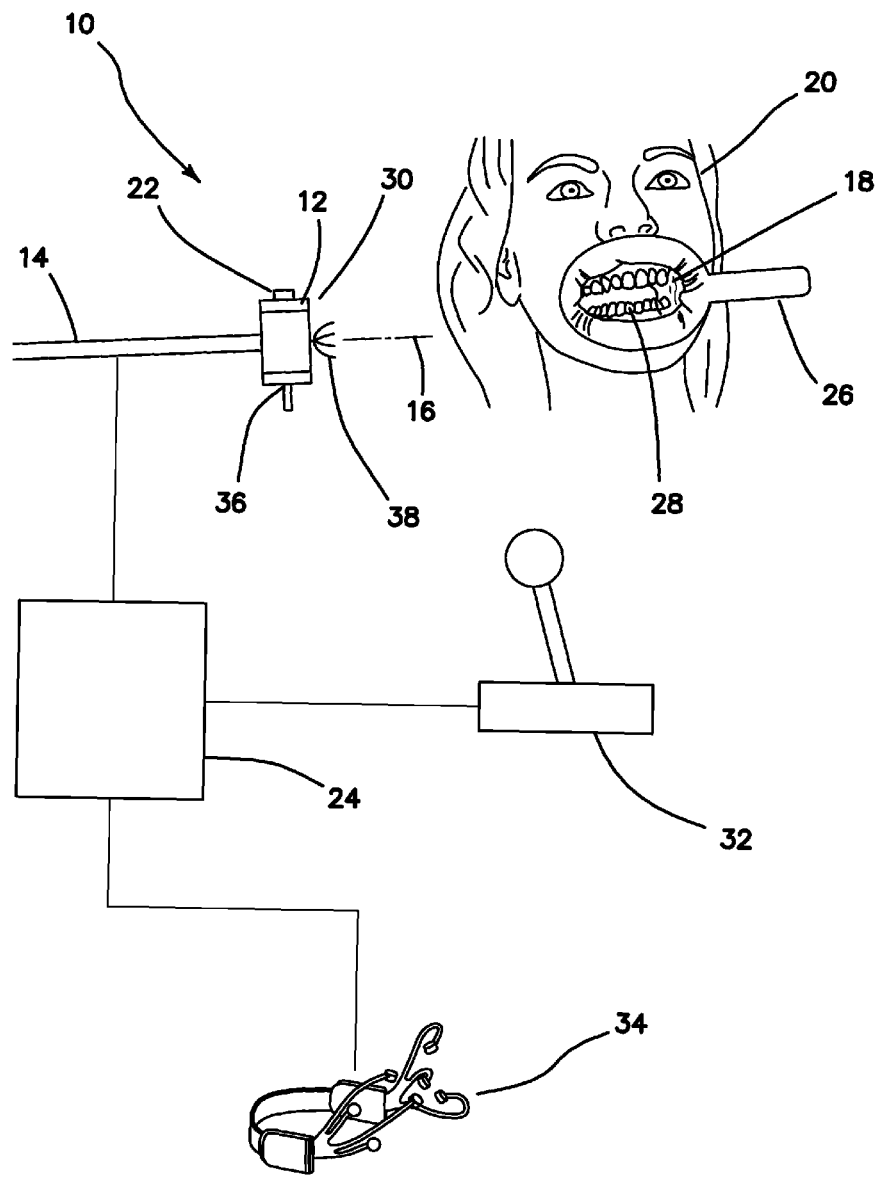
FIG. 1 is a simplified diagram illustration an embodiment of the illustrated invention.

The illustrated embodiments of the invention pertain generally to methods and systems using a video camera on a movable mount above a patient to zoom in on teeth, including mounted microscopes. The embodiments re referred to as an exam-cam system. As diagrammatically shown in FIG. 1 the illustrated exam-cam systems 10 comprise a miniature camera 12 on the end of an arm or stem 14, capable of rotating 360 degrees around a defined axis 16, and able to fit on its arm or stem 14 into the mouth 18 of a patient 20. The arm 14 includes sensors 22 which are coupled to a computer or controller 24 for avoiding any collisions with the teeth 28 or the interior of the mouth 18 to avoid injury to the patient 20, who typically is positioned with a cheek retractor 26 in place. Sensor-controlled programs stored in controller 24 allow the camera 12 to track and compensate for any small movements of the patient 20 to keep the camera 12 in a constant relative position to the teeth 28 if elected by the dentist.

The camera arm 14 has its own intraoral lighting system 30 mounted in a position to illuminate the mouth 18 without swamping the camera image, and is maneuvered by a joy stick 32 or a headset peripheral 34 similar to a game controller like that sold under the trademark, Emotiv® by Emotiv Ltd of Hong Kong, which programmably learns subtle head and facial muscle movements, or muscle activation, and which is worn on the head of the dentist to control translational and rotational movement system 10. In this way the user or dentist is able to peer into the mouth 18 and maneuver camera intraorally by small facial and/or head movements as if he or she were riding on the camera 12 itself and looking at various sites on teeth 28. Control of the distal end of the camera arm 14 using an eye tracking sensor alternatively included in headset peripheral 34 to track the eye movements of the dentist is also contemplated as included in the illustrated embodiments.

The system 10 also allows the patient 20 to be treated robotically. The arm or stem 14 is also arranged and configured to include a "gripper" 38, and/or "tool" 36. The tool 36 could broadly be anything from a conventional rotary instrument (dental drill) to dental laser or to abrasion tool to cut tooth material or trim soft tissue. The gripper 38 is a mechanical clasp or activatable mechanism which has the ability to grasp the buccal and lingual surface of the tooth close to the gingival (gum) margin or as far away from the operative site as possible. The arm 14 moves with the patient 20 once gripper 38 couples to the teeth 28. System 10 then aligns its camera image to match a previously scanned image of the dental area in view, including using images originally captured on a cone beam computer tomographic system (CBCT), laser or other optical scanner, or even with conventional impressions. If the area in question is a single tooth and the operative area is small, the gripper 38 attaches to the tooth in question. If not, the gripper 38 affixes itself to an adjacent tooth or to one on both sides of the operative tooth or area.

Figure 2A:
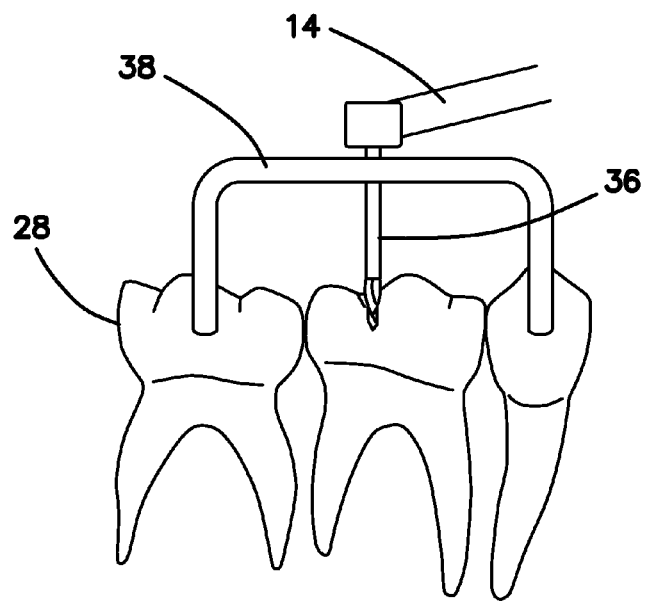
FIGS. 2a and 2b a diagram of the tool and gripper wherein are combined into an integrated assembly in which the gripper guides the tool with respect to its position relative to a tooth or relative to adjacent teeth.
Figure 2B:
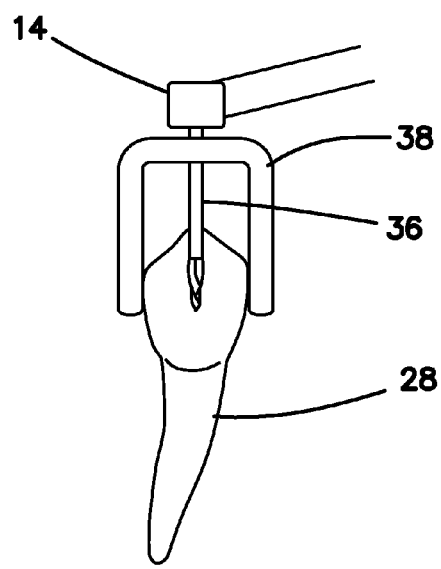

In one embodiment the gripper 38 and tool 36 may be combined in an integrated assembly as shown diagrammatically in FIGS. 2a and 2b. In FIG. 2a gripper 38 is adjustably coupled to the distal end of arm 14, gripper 38 is a U-shaped fixture and extends to contact or grip two nonadjacent teeth 28, e.g. the buccal side on one tooth 28 and the lingual side of the other tooth 28. Tool 36 in this embodiment is a drill or other rotary dental tool and is controllably coupled to gripper 38 so that it is selectively positioned relative to the two opposing ends of the gripper 38 and positioned to a tooth 28 between the two nonadjacent teeth 28 with which gripper 38 makes contact. Tool 36 may, for example, be coupled to the lateral extending arm or platform of U-shaped gripper 38 by means of a rack and pinion gearing combination or other controllably adjustable coupling.

In the embodiment of FIG. 2b gripper 38 is again adjustably coupled to arm 14 and formed as a U-shaped fixture, but is dimensioned so that the two opposing ends of gripper 38 contact or engage the buccal and lingual sides of the same tooth 28. Again, tool 36 is selectively positioned relative to the two opposing ends of the gripper 38 and selectively positioned relative to tooth 28 between the two contacting ends of gripper 38, which is coupled to the lateral extending arm or platform of U-shaped gripper 38 by means of a rack and pinion gearing combination or other controllably adjustable coupling.

The system 10 then robotically performs a dental operation or procedure, such as preparing a tooth for a restoration, reshaping the edge, or adjusting the "bite" using data similar to what is produced from conventional three dimensional digital scans such as those provided by the imaging systems offered by Orametrix of Dallas Tex., Imaging Sciences of Hatfield, Pa., or Cadent of Carlstadt, N.J. to mention only a few.

Further embodiments are arranged and configured to adjust orthodontic wires with the microgrippers 38, place braces, and apply coatings with tool 36. Another use is to robotically "drill" bone using tool 36 for precise implant placement. Several prior art systems currently produce a cad/cam template to guide placement of tool 36 or gripper 38. The illustrated embodiment of the invention eliminates that step of developing and using cad/cam templates by allowing the drilling to be precisely placed and robotically done.

Therefore, in summary it is to be understood that the intraoral robotic system 10 of the illustrated embodiments provides:

a. "robotic occlusal and incisal adjustment", which includes, but is not necessarily limited to:

A. a caliper or gripper 38 that grasps the buccal and lingual of the tooth and lines up on the tooth anatomy/image;

B. a robotic shaper 36 which adjusts a tooth based upon precise digital occlusal analysis; and C. an arm 14 which is operated by a joy stick 32 or headset peripheral 34 to allow the dentist or user to visualize the patient's mouth 18 just as if they were sitting next to the patient in the chair (which they might be), but at a high degree of magnification, with customizable imaging enhancements and without bending over or looking with mirrors.

b. Robotic tooth adjustment/preparation or implant preparation/placement:

A. a gripper 38 which holds the buccal/lingual of the tooth or teeth medial and or distal of the tooth or area to be adjusted or prepared.

B. a gripper 38 which senses and adjusts to any patient movement;

C. a camera 12 which aligns the image of the scanned tooth with the actual tooth, correlates this to the gripper 38 and the cutting device 36.

D. a robotic dental cutting device, rotary, laser, abrasion-dental device 36, which prepares the tooth or area.

E. an imager 12, 24 for rescanning a prepared tooth to assure it matches intended preparation or adjustment.

With this technology the practitioner or orthodontist can one or more patients 20 remotely, sits in one location and looks at one mouth after another, and details the changes. The microgripper 38 bends wires within the mouth 18 to make adjustments, making them small enough and precise enough, with pinpoint heat application, to make adjustments without removing the wires, while tracking them precisely.

If appropriate, data is sent to lab or milling machine to fabricate a restoration to fit the preparation, no additional scan or impression is required. The same technique is used to adjust the restoration once placed, if required.

Many alterations and modifications may be made by those having ordinary skill in the art without departing from the spirit and scope of the embodiments. Therefore, it be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. An apparatus for intraoral imaging of teeth of a patient comprising:
   a robotic arm;
   a camera coupled to the robotic arm;
   a gripper coupled to the robotic arm;
   a tool coupled to the robotic arm;
   at least one sensor coupled to the robotic arm to sense the relative position of the teeth and/or mouth with respect to the camera coupled to the robotic arm;
   a controller coupled to the at least one sensor and the robotic arm, the controller configured to control the robotic arm to avoid any collision between the teeth or the interior of the mouth and the camera and/or the robotic arm; and
   a headset peripheral coupled to the controller, which headset peripheral programmably learns head and muscle movements, or facial muscle activation of a user to control intraoral translational and rotational movement of the robotic arm,
   wherein the headset peripheral is capable of controlling the rotational and translational movement of the camera, gripper, and tool coupled to the robotic arm by selectively positioning the camera, gripper, and tool coupled to the robotic arm intraorally and providing a selected remote visualization of the teeth of the patient to the user, and
   wherein the robotic arm is configured to be selectively moved by the controller to track any movement of the patient and keep each of the camera, gripper, and tool coupled to the robotic arm in a constant relative position with respect to the teeth or mouth of the patient while the headset peripheral provides the selected remote visualization of the teeth of the patient to the user.

2. The apparatus of claim 1 where the tool comprises a rotary dental instrument, a dental laser or an abrasion tool to cut tooth material or trim soft tissue.

3. The apparatus of claim 1 where the gripper comprises a mechanical clasp to grasp a buccal and/or lingual surface of the tooth close to a gingival margin or at a predetermined distance away from an operative site.

4. The apparatus of claim 1 where the controller robotically controls the camera, gripper and/or tool to prepare a tooth for a restoration, reshape an edge, or adjust a bite using data from a previously prepared three dimensional digital scan of the tooth.

5. The apparatus of claim 1 wherein the controller robotically controls the camera, gripper and tool to adjust orthodontic wires with the gripper, to place braces, or to apply coatings.

6. The apparatus of claim 1 wherein the controller robotically controls the camera, gripper and tool to perform robotic occlusal and incisal adjustment.

7. The apparatus of claim 6 where the controller robotically controls the camera, gripper and tool to perform robotic occlusal and incisal adjustment by use of the gripper to grasp a buccal and lingual surface of a tooth and line up with a previously prepared tooth/anatomy image.

8. The apparatus of claim 6 where the controller robotically controls the camera, gripper and tool to perform robotic occlusal and incisal adjustment by use of the tool as a robotic shaper which adjusts a tooth based upon precise three dimensional digital occlusal analysis.

9. The apparatus of claim 1 further comprising a joy stick or headset peripheral coupled to the controller, where the controller robotically controls the camera and the robotic arm as operated by the joy stick or headset peripheral to allow a user to selectively visualize the patient's mouth just as if the user were sitting next to the patient.

10. The apparatus of claim 9 where the controller robotically controls the camera to allow the user to visualize the patient's mouth at a selected magnification with user-customizable imaging enhancements.

11. The apparatus of claim 1 where the controller robotically controls the gripper to hold a buccal or lingual surface of a tooth medial and or distal of the tooth or of an area to be adjusted or prepared, while sensing and adjusting for any patient movement, using the camera to align a previously prepared image of the tooth with the actual tooth as imaged by the camera and correlating the images to the gripper and the tool, which includes a dental cutting device, rotary, laser, abrasion-dental device to prepare the tooth or area or using the camera to rescan a prepared tooth to assure it matches intended preparation or adjustment.

* * * * *